United States Patent
Yoon et al.

(10) Patent No.: US 10,722,544 B2
(45) Date of Patent: Jul. 28, 2020

(54) STREPTOCOCCUS INIAE BACTERIOPHAGE STR-INP-1 AND USE OF THE SAME FOR INHIBITING THE PROLIFERATION OF STREPTOCOCCUS INIAE

(71) Applicant: Intron Biotechnology, Inc., Gyeonggi-do (KR)

(72) Inventors: Seong Jun Yoon, Seoul (KR); Soo Youn Jun, Seoul (KR); An Sung Kwon, Gyeonggi-do (KR); Hyun Min Song, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 293 days.

(21) Appl. No.: 15/766,497

(22) PCT Filed: Sep. 30, 2016

(86) PCT No.: PCT/KR2016/010954
§ 371 (c)(1),
(2) Date: Apr. 6, 2018

(87) PCT Pub. No.: WO2017/061733
PCT Pub. Date: Apr. 13, 2017

(65) Prior Publication Data
US 2018/0303885 A1     Oct. 25, 2018

(30) Foreign Application Priority Data

Oct. 8, 2015 (KR) .................. 10-2015-0141281

(51) Int. Cl.
| | | |
|---|---|---|
| *A61K 35/76* | (2015.01) | |
| *A61P 31/04* | (2006.01) | |
| *C12N 7/00* | (2006.01) | |
| *A61K 8/99* | (2017.01) | |
| *A23K 10/16* | (2016.01) | |
| *A01N 63/00* | (2020.01) | |
| *A23K 20/158* | (2016.01) | |
| *A23K 20/20* | (2016.01) | |
| *A23K 20/163* | (2016.01) | |
| *A23K 50/80* | (2016.01) | |
| *A23K 10/18* | (2016.01) | |

(52) U.S. Cl.
CPC .............. *A61K 35/76* (2013.01); *A01N 63/00* (2013.01); *A23K 10/16* (2016.05); *A23K 10/18* (2016.05); *A23K 20/158* (2016.05); *A23K 20/163* (2016.05); *A23K 20/20* (2016.05); *A23K 50/80* (2016.05); *A61K 8/99* (2013.01); *A61P 31/04* (2018.01); *C12N 7/00* (2013.01); *C12N 2795/10321* (2013.01); *C12N 2795/10332* (2013.01); *C12N 2795/10371* (2013.01)

(58) Field of Classification Search
CPC ............ C12N 2795/10321; C12N 7/00; C12N 2795/10371; C12N 2795/10332; A61K 8/99; A61K 35/76; A23K 10/16; A23K 20/20; A23K 50/80; A23K 10/18; A61P 31/04
See application file for complete search history.

(56) References Cited

FOREIGN PATENT DOCUMENTS

| KR | 10-2002-000217 A | 1/2002 |
| KR | 10-2012-0067096 A | 6/2012 |

OTHER PUBLICATIONS

NCBI, GenBank Accession No. KP208803.1: *Streptococcus* phage Str-PAP-1 (2014).
Richards, G.P., Bacteriophage Remediation of Bacterial Pathogens in Aquaculture: a Review of the Technology. Bacteriophage. 2014; 4(4):e975540 (12 pages).
Wright, E.E. et al., Induction and Characterization of Lysogenic Bacteriophages from *Streptococcus iniae*. J Appl Microbiol. 2013; 114(6):1616-24.
International Search Report dated Dec. 16, 2016 by the International Searching Authority for Patent Application No. PCT/KR2016/010657, which was filed on Sep. 30, 2016 and published as WO 2017/061733 on Apr. 13, 2017 (Inventor—Yoon et al.; Applicant—Intron Biotechnology, Inc.) (Translation Only—2 pages).

*Primary Examiner* — Satyendra K Singh
(74) *Attorney, Agent, or Firm* — Ballard Spahr LLP

(57) ABSTRACT

The present invention relates to a Siphoviridae bacteriophage Str-INP-1 (Accession NO: KCTC 12687BP) that is isolated from the nature and can kill specifically *Streptococcus iniae* cells, which has a genome represented by the nucleotide sequence of SEQ. ID. NO: 1, and a method for preventing and treating the infections of *Streptococcus iniae* using the composition comprising said bacteriophage as an active ingredient.

2 Claims, 2 Drawing Sheets
Specification includes a Sequence Listing.

SEQUENCE LISTING

<160> NUMBER OF SEQ ID NOS: 1

<210> SEQ ID NO 1
<211> LENGTH: 33269
<212> TYPE: DNA
<213> ORGANISM: Bacteriophage Str-INP-1

<400> SEQUENCE: 1

```
ttaatccatg cttcagccat taacctacaa ttttcgtcac taccaaaaat ccaatcaaaa      60
atttttgcag gcatatcgct gttagaaaac aagcctgtta atgttaaagc acgcttttg     120 caatactcta tccaatccgc cacaaactgc ggaacttctg gttttggttg gtcgatgtca    180
ggctcatcta atctaaaatc actatctgac atgtaataaa tatcgtcttt aattaagcaa    240
tccagctcgt taacatttct ttcactatcg aggaaatcta tgttgcccat actgtcaaca    300
tatcctctaa cccaaatctg tgtacctcgt tttaaatctt caatcttcat ttgctacctc    360
ttttaatact tttgtaaaaa tttccttaac tagtagttgt ggtatatttg atcgctcatt    420
atatgacctt gaaaaatctt ttttaaaatc aatttcattt ggaatgtttt cgtgttttaa    480
attcaaatca atattcccgg aaaatcgtgt tggtttactg attggataat cataattgtt    540
atagtaagta aaatttacat atggtaattt aaatccttgt accagttcga tatactccca    600
aattctgcca aaagctgggt tttctataag atagtatttt ggctcatatc gctttatgat    660
ttccaatgcg ttgaatactg ttaactctcc attgatacgt tttataaaag attttttccgg   720 tttaaattgg tatctatcat aatctgaatg atcccttact gtaaacctcg ataagggtat    780
ttgaggttcg aacaatccat caccctttc ttgtttccaa caagcgtttc ctctatccat     840
cgcactagca acagaccaag actcgcacgg agggctagcg ataattaaat ccggctttgg    900
taatttatct aatacatcaa acaacttagt gtctccaaac aacctaccgt aatcagctaa    960
attcaaatta ataaaatggt cgtttttgtt ttcaatatca attccgattg gataaatttc   1020
tattcctgga aattctttag ccgctttagt ataagatcca ttgccactat caaataacgc   1080
```

```
ccaaacaatc atcttcatcc cccattccca gtaagttctg caattcgttt tgtcttatca    1140
gctgattcct cacttacttt tttaagctga tactgcgttc tgtctagttg accagtaagc    1200
cctttgattt gttggtcttt tgatttaagt tctgttttga ggtggttatt acgttgtttt    1260
aattgattat tttctttatt aacagtactg caagcgagca taatgcaaat aacaagtcct    1320
aataaaacag agttgagcca agacaaaaaa tcatttttca ttccacttcc tccaaccaaa    1380
ctgccaacat catgcaataa ttagccatgt cgtttaacgt gtctgaaatg ctctctaaga    1440 cttttgttttc attcttggta agattgacca gtcgtctgta tttatcgctt atacggacga   1500
taccagccac ctctccgaac tcattcaacg attcttcaaa cgaattacca taatctgcat    1560
tcttcttcaa aaacgtttga taattttcgt catatacttt ttgcattgat tctgcgttta    1620
tcttatccat tcatcacctc gtacttatat acctgcggtc taatattaag ctgacttgca    1680
taagcctcag cttcttcttt tgtcgcaaac tccttgtcct cgtaaacata ttcacgacca    1740
aacttcttgc gtttaaattg tctaactttc cacgttgcca tttacaatcc tcaatgcatc    1800
gtctacactt cttgccacac ctgcaagcgc tccacgactt tgcatgtttt ctataaattt    1860
tttctgttct ggtcgcactc gaccttttc gttttttact tcaataaaga atgcctttgc     1920
atctccttta cggaatccag ataaatcaca atatcctta ggtacaccag tttcaaacca     1980
tctgccattt tgcattttaa ctttaccgac gtttatccta aatactgtgt gacctgcttt    2040
tgatagtcca actctgattt ggttttgaat tgtgtgttct tgtgtcattt tcctcctaaa    2100
agttaagggt actgttaacc acttataaag tcagtcatac caagcgatta gaccattatt    2160
tttaaaaaaa gttaaaggtt aatagtcttt ttatacttat atatatattt atatatttat    2220
tattattatt aattaataga atatagagtt aactattaac cttaacttgt ctaattactg    2280
atatataagg ttttttaaacg gttaagggtt accattttc cattaaccaa actattaacc    2340
attaaccttg atataacatg taactggttt tttcggatca ttttcatcgt gccaagaaaa    2400
aactcctaat tctgttggtg tatccacact aggcataaat ccaattggtt tagcaacttt    2460
cttttcccac tctcctgtta aaaatgtagg cagttgcttt tcaaacttaa atttatttaa    2520
cgctacaatc ccagaatcct tgcaccatgc tttatacaac caccacagga atttactagg    2580
tagtctcttt gattcaaatt taggaaacca ttcattgacg aatgctttaa ctgtgtcatt    2640
tgattcttta aactcttcta gctgtacttt agttgctgac ggttcactaa acttattgaa    2700
attaatttca agagcttttt ttaaaacata ctctctaaca tcttctctat aaatatagtc    2760
atctttaatt gcccagttat cttctttagg tgaaaatgtt tttctaaaag gtataattgt    2820
aaatcgtcga taagtaccat ttgatttatt tttaaatcga ggcaattcat ttgttgattg    2880
aataactgtt tttctaaaga tagtcgtata aggttgttta ttcttttcct ctactaatac    2940
tggttcacca gtgacaacag agttgaagtt agatgattcg tctacatata taccagcttg    3000
cacatcgtca ccgataatta ctgttttacc ttcaatcatt gataaggcaa atcgttctga    3060
aaattggttg agctttaatg ttgcaatgtt ttttaaacca attacattag ttataagctg    3120
ttgtactgta cctttaccgt cattaccttc accaacaaac catattgatt tgcggtaaga    3180
atagtttcca tttaacgatg ctgatatgac ttgccataat aaatcgacta actcttgatc    3240
gttatccatt aaatctaata accagctatc aacatcccaa ccgtcaataa caggggactt    3300
agcgaaagca tcatattctg tcgcaattgt cgaaaatgcc acaaattgat gagtaaaccc    3360 taaaagttttt tgttctttttt tgtcatatat accgttttc actaatataa accgttttgg    3420 attttttaaaa tcaccaattg aaaaattaca ggagaatcca tcgtatttat gaatcctatc   3480
```

```
atttgaagaa agcataaata aaacattttt agcttttgt tcgttaaagg ttggttctaa    3540
caaccgaatt actttatagg caaatgatgg gtctttgtga taatatccgt tatcaggatc    3600
ataaacagca accctcccat ttgataatgt aatgatgtaa agtaggtatt ccataccttg    3660
agacaccgct aattcattta atgttgttcg ttttgtatct ttttcttgcg cagtaccatc    3720
ttcatttact tttgagttag cttttcaag ccatctatcg cgataatttt ttgcacctaa     3780
tttaatttcc ttccaatcgt taggcctttg ctcgtatata tcgattattt tattttcgta    3840
ctctgcttta atagcttgta tattaactgc cacttcttct atcaagctcc tttctcaaca    3900
tactctcata tgttgcatca acttcgcttt ctggcaacgg gtttggtgtg taatgattag    3960
caagcaatgc caacttatat actgcttctt cgtcaacacc tctgagcaac agtccgccta    4020
ttagacttgc gagtgaattg tttctaccac cagtatcccc tagaccaaag acaatttttt    4080
caaataattt agcagtctga ctactgtatc cactattacc attactactg aaatcccttg    4140
caaccgtttt tcttgtatgg ccaattaatt caatcaattc atttggcgct tctgcgaatt    4200
ttccaccttc aagtgaattt tcttatccc aaatgtaact acctttaat gtatttgaag      4260 gagcaaccaa gacataatta ttgtcattgg ctttgatatc gacaccgtct aaaaaaccaa    4320
cactctggtt aattgataca ccttaggct tcttaagaaa aatatgccta cccccagtag     4380
gggtgatggc ttgagttgtt ttaggtatta ggtcttacc ttcccaatta ttaaaacttt     4440
caaagccatc aacatcacca tggacatcta tgtcaattac aaaaagtca tctgttctta    4500 ctgcaatatt tgcatcggga ttttctttcc ataataattt gatttcatgt tcagtaaacg    4560 attattttt aaattttgtt aatggtcgtt tactttttt atcaattgga atgacagaaa      4620
atccgttctt ctgataatgc agtgcataat ctaccattcc tgcaatcata ttagaatggt    4680
aggctatctt cgattgattt ttgattagga atcttgtcag ctaattgtga tgattccatt    4740
gacttaatgt tcaatcgatt tgttacttta ccttgatatt cattatcttc atttttaact    4800 gttacttta atgcttttcc acgaatctga tctaagaaat ctttttctga ttcaattact    4860
gctgatggtg gaaattcaat tgctttagca tattgttgta aacggaactc taatggttta    4920
ccttctgctt ttgaatacca gatacggtca aaaattaatt gattgtgaaa ttcttgtttg    4980
aaatcatcac ggatctttag gcggatatct aagaagtctg atccgcttgg tgttgctgac    5040
tgttcagcgg tatctacaaa tacctcataa gttccgtctg tgattgatgc gaattgttgt    5100
gcttttgaat aatctactgt gaataatgac ataattttat ctccaaattt cttttctttt    5160
ttgtttatag taaatccacc cttttttata attgtggata agtgcgaatg cttgtaattc    5220
tggtaatgtt tgacattgtc gccaatcttt accgtatttt ttaactttag aaaaaactgc    5280
atagtctttt ggactcattt ctacattttt tccgtttaat tcaatctcaa tgatttcatc    5340
aactctgact agttcaccgt taacttttt catttctacc ttttaggtt cttcttttaa      5400 tttttcgcca cagtacggac aacatccgtt aactatatca gttgagaaga acgcaccgta    5460
acatttagga cattctcttg tagctggtga atcgtcttta tcttttgatt tttcttttt     5520 cccttcaaga gtccaattcc tatcttgatt aggaaaaccg tggatttcc aattaccgac     5580 atgatcaatt aatattgctt ctttaccatc tcgtggattc aatgcgcgca ttgcaaattg    5640
taagtacaat gataatgaag ttgtaggtcg taacataatg catacatcaa catttggtaa    5700
gtctattccc tctgtaaaaa ggtttacatt caccattatt agtaagtcac catttctaaa    5760
gtctttcata gctttatctc taatttcctt aggtgtacta ccatgtatta cagctgatga    5820
```

```
                                      -continued
ataacctctc tcagaaaata ctgttgctat ttctgttgct tttactacag aacttgcata    5880
aacgattgct tgttttcctt tagctaaatc ctcataatgt gtgacatagt caccgttaac    5940
cattttccag ctatctaatg attcatctat tgatttaact gtgtaatcac cgtgtgattt    6000 tttaagttttt tctttatcaa tcaactcaag tgaataatat cgatattttg aaatattacc    6060
ttggtcttgc aaccactttta tagatttacc tacaactaaa tcatctgcca tatctttaaa    6120
accagaacca tctaatctta ttggtgtacc tgtaaaaaat agatgatagg ctttatcaaa    6180
ataattcaat atttttttgat actgttttgc tttgatatga tgcgcttcat ccactaaaat    6240
gatttcaggt ggtggtaaat tttctagttt tctaaccaaa ctccctacag tacctattgt    6300
taataagcct gtattaacac cattacgatt aaacgtttcc ttaacttgat cgtttatctc    6360
ttttcgatga ctgaaaaata atacatggtt cctttgtct gtagcacctt tagcaatatg    6420
agccattaca actgtcttac cgcttcgagg aggtgactga accattatgc gacgattacc    6480
tttaagaatt gattgcccta tgttagctac taattcttct tgataatctc ttaaattaat    6540
tatttaaatc acctccaaaa ttaaacaaat cttcaatctt gcatccttttt ctatcatcta    6600 aacgattttt tgcatataca cttgctgaag gttgtaagat aaaacctcta acttcttctc    6660
catcatcagt tatcttttta actaaacgag ctacgacatc tgtaagacct agaaagttat    6720
ttagaatttt ttctctaata tcaggcattg cgcggttata aatcattccg ttttcatcag    6780
tccatttatc cgaagactcc catgcaataa atacaatacg tttgttaagt tgtaataatg    6840
cccgtaaact atctaaaatt gtaaagtcaa cgcgttggta atcagcttga cttggaactc    6900
tgtgattctt tccatctctt ccgagatttg ctagacaagc tctaaacagt tcagaaacat    6960
tgtctacaac tatgttgtca tattctttag ctccgccttc aaccaattca ttcactagcg    7020
ttagccaact ttcccagatt ttatgtgtat caacgtcagc aatatcaata ttttaatac    7080 ctcgtaaaac ctttgctgac ttgtcaatat ttacaacaag tgttttacct gataaatatt    7140
tagcagttga tgttttccca taacccggat tcccgtaaat taaataacac gtatcattaa    7200
tttttaaatc tgttgcttta gttatctcca atttctaatc cctccacaaa atcgtgagca    7260
gcatttctat aatcaaattc attccgttgt tgcctatatt tttctttgaa taattcatct    7320 actactttttt tgtttaaata ctccgaatat tcatctgcta aattgtcagc aaaatcattc    7380
atccgtctat ttatttcatt ctcaattttta gtatcgaata aatcaatttt gtcggatgtt    7440
atatctccat gtttgcagtt gtaactcggt actatttgaa ttttttccgaa acttgtcatg    7500 tacgttctat aattttttcaa tcgtatgccc tcgcttgcca cgttactgtt ggttcgtctt    7560
cttcgcagta aggacaattt aaatctctgt aatcagaaat gttttcccaa gccttacagc    7620
agtttgtgca ataatattct ctaactagca atatgattcc tttctttaaa gtcgttaaca    7680
acaacatcga tgttatataa gtcctctgtc atttcttggt tttcttttaa aactaactca    7740
taatcgttta ctaattttttg atattctagt tttaatttaa agttttcatt aattaaatct    7800
tgtgtgtcta aatgtacttt atcgtttctg attttttgtta atccatacag ataagctaaa    7860
tctatttcaa agtaatcagc aatacttgac cagaatgcag tctcattcat gttgattgga    7920
ccattttcat aaacttccca ctgcttagca ttaattgtcg gcgcaattag ttttatttct    7980
ttaattaatt gatctagtgt aagtccacgt tcttgtctta gttttttaag attgttcata    8040
tgtcacctct aaaattgctt tcttaaaatt aaccaacata tcatattctg attttgaaat    8100
tgttatcatt tcttctgttt gttcattttct gatatttgaa taaccaagta aataagaaac    8160
tgatacgtta aaataaatttg ataaaactac tggattaact cctttaattt catgtttccc    8220
```

```
attttcccac cttgaaatgg ccattttga gatattcata attttttccta attgttcttg      8280
tgtcatacct ttttctaacc taagttcttt aagtctattc atttagcacc tcgcatataa      8340
gagtggaaag catcgtattg cctttctgac gacaaacgta aagtatcgtg tggtttaatt      8400
tgcacttgtt tttcttcttt agcaaagatt aaattaaata ttttttttcat tttatgctcc     8460
tgtgtcaaat ccactatttc gtaaaaatct gtggaagttt gctagataag attagtgagt     8520
atagaccaga ttcgttgatg atagtcatgc tttgagttcc accaagggtg ccctgaattg     8580
gggcgtcctt tttatcttct tcatctacat gactagcaat tgcatttctt gcttttgcat     8640
atcctagtcc ttgcctacaa agtaaggttc gttgttaatt gttactgttc ggacttcttg     8700
tcctttatgt tgttcctttc tagttcacgt tttgtgaagt gttatcgata aaaatttcgc     8760
taatactttt atgaaagaaa ttagcgattt tgaacatttc cgatgatgaa aaatcagttc     8820
tcccgagttc tttgtttcgg tacgatacag atgatttacc aataacatca gccagctttt     8880
cttgagaaat atcattttgc tttctcaatt gatataacac aatttgcatt tgtcccaaat     8940
tgttctcctt tctagtattt agaattatta agctttcctt gagcttgatt atagtatact     9000
ccacaatttg tgaagtgtca acagttttct ttctaaaaaa taaaaaaact tttcaaaacg     9060
taagaataat gatatgataa ttttgtgata ttcaatagta aagaggtta aaaatggacg     9120
aaaaagaaat taataaattt gttgggaata aaataagata gcttagattt gaagaggat     9180
taactcaaaa agaactcgct gaaagaatag gtatgggaga cacaaccata gctaattacg     9240
aaatccatta taaccgccat tatgctaaat gtccgtttaa atagactaaa aataatttta     9300
aaaaagttga taaaaacgct tgacattata tacaatattg tatataataa gtatataaag     9360
ataaggaaac gaggaaaaca aaatgactta cgataaatca ggaattatga cacaagcttg     9420
gacattattt aacagtgata atttcgatac ttgtgactat gaatacgcta ctgctttagt     9480
atatggtcaa aaaactttct ctgactgtct taaagaagct tggggtcgtg aaaaagctat     9540
cgttgaaaga atggctgaaa agaagctaa tgctcctctt tctgaagaag ctaaagcttg     9600
ggattgggct tgtcgtaaac ttggcgtaac tgctgaagta accgcagtag aaaaagttcg     9660
ctacgttgac gacatggcta agaaatgtg gtcaacaaat gtttggaaac aagcaatcaa     9720
agcagttcaa ttatatgcta ctgttgcata aaaaaggag gaattatgaa agctgatgca     9780
aaaaaaataa aatggttatt ggaaatgag actcaatata aatctcaaa agatacaggt     9840
gttgcacaat caaaattgtc atctttaaaa aatggcaaaa taaagctcgg gaatatatcg     9900
ctagaagttg ctagcaaact aacaaaatat tccgaggaaa ttcaaaaaaa ttaaacaaat     9960
ctattgacaa gatatataat attagatata ataagtatat aaaataaata aacaaaagag    10020
gaaaacaaaa tgaaaacta cgaagtaact aacgaagcta aaaacttaaa cactcaagtc    10080
gaaacaatgg ggcaagcagt tgatttatat aaacaatacg gttctgatac aattgtttgg    10140
agtattgaca aaaacgaaga tttaattgat gaagtaactg aacttgttgc agaatatgct    10200
gaaaaaggca cagtaattaa ataatatgac tgctaaaaat gacttgacag gacggcgctt    10260
tgagcgcttg actgttttag gtgatgttgg caaacgagcg aaaaatggta aggttttgtg    10320
gcattgcatg tgcgactgtg gaaaaataac atttgttcgt ggtgatcatt taaaaaacgg    10380
aaaagttaaa tcgtgtggtt gtctaaatga cgaccttaaa agaaaaaggt ataagatttt    10440
aattggatat gaaaacgata attttaaagt tatcgtcaaa aaagaaagtg aaaatcaacg    10500
tgtcgattgg ctttgtgaat gcaagcattg cggtaattac acatatctca attcaaacga    10560
```

```
aagtgaagtc acgaaatcat gcggttgttt gctaggtgca tcaaaagaat ttatgaacgc    10620
tatacgagat cctgaatctt taaagtcgac aaaaccgact gctaaaagca caactggcgt    10680
gcgtggagtt tattacaata agcgtaaagg taaatatcaa gcatttatta atgttgataa    10740
gaaaacagtt tatcttggcc aattcgcaag attagctgac gctgaacatg cacgaaaaaa    10800
tgcggaacaa gaattttgga ataaataaaa aaagcccaca ctgattagtg agggcttttc    10860
ttatatctta ttaagtttaa atccttgaat gtatctgacg tgagcttaga atgaaactta    10920
tcgcaagtgt tgataatgca gatgtttctt ttaaataaca caaaaaccg ccctcgaatt    10980 gagagcggtt ttgattatgt caatattgac aatctattat ctaaaagtac caaaattagt    11040
cacacgtcgg ccattttgtg agtttccgac cgcaacatat cgtctaacac cagtcacgct    11100
gacatatgtt acccaaatgt aaccatctga atctaaccat ccatcatagt taaattccat    11160
gttttctccg tatgtagcaa ctatttctgc atctaggcga ggcgcagagc gaacgtttaa    11220
agctgcaaca cgaacagtaa atgtaccagt ctcaggattg gcaacataag taccatctga    11280
ttctgattta actggtgcgc ttgtttctaa ctgttgtgct ggcgtactat cgtaaggagg    11340
ataaaaccaa cctaaaatat agccagtgcc gtcagaaaat gagcgattga tgtatcgtgc    11400
aggtccacca aattgtaact gatcgttgat accatctcca ttattatcag agtagccatc    11460
aacattttgc tcgatagtgt ataaaatata accatcagac gttttgatta ctagtccagt    11520
gtggccatat ccatgagcgt aagttaccat tacaaaaata gcaccatctc ttgggtttac    11580
gccaggttca tcaaacacaa cttccattcc ttgagctttt gcgctgtcga gtaagtcaat    11640
agcattgccc caaagtgcca caccaaaata ttttgttgta atccagtttg gcaggtcaac    11700
acattgtgtt ccccaaacgc cgtccaggtc tacaccttga ccagtatctg ctaaattttt    11760
agcaaatgca attacttctt cttttgttgc catattattg acctttccag ctgtcattca    11820
tgcgtttaac tgctgcttcg ataaacattt ccatgtcttg attacttaga tatacattgt    11880
gcttagacag ctcgctttgc atgcttattt tagcttctgt gagcttgtct agacctttga    11940
tgtctttatc ataagcaatt tgttcaactg cctcaacggc gttttagcg acaatttcag    12000 caattttaac tgctttttcg ccacccttt tgagtaaata ttctttaact tgcttaacta    12060
caataccagc taaaatagtt aaaattgata gcgctgaacc tgtaacaata ttagtaattt    12120
cttgcatgtt atttcctctt ttctatgctc tccattcggt cactgattct gaccatttcc    12180
gattgtatgt ctccgactgt gttagcaatt tcccctagtt gggtagtggt ttttcgagg    12240 tgattaagca atctttcttc tctgacattg ctttcagctt tcgattgctc gtggaaatcc    12300
atgagctttt tctcacgttt ttcagatgtt tttattaaat agctaacgac aaaaccaaat    12360
aaaataataa ataaaattgc ccacacagct tgacttgttg cgattctttc cgcttgctct    12420
actgtcacat agatacctcc tttacgtaga tttaatggta ttattccact cttcaatctt    12480
gatattgtct tgtactgacg tatctaattg actgccgagt ttgcacgaac tgatgtaaat    12540
aacattcata taacttgtgt atgttccatt tttgctgact gaaagtctat ttttaaattt    12600
gctatttgta actttcatga tgcaatttcc gcgttgtgct gagctaggat tgacagattt    12660
tgagtggtaa gatacatcag agtgcatctt actctcaaac acgcagttgg tagcttcgat    12720
gtaaccctca tctccaaacc ctcctccgat acattgagga gcgagtaaga cagatgacgg    12780
aaccgagttg tgaatcaata ctaaatcttt gtagacgttt ttgtaaaatg gtgaataacc    12840
accgcctgat acacccatgt catcgtgtat acagtaccta caattcgaag caataatagt    12900
taacccgtag atttctgatc cagtagagcc agcaagaata ttaagtggag acaatagcca    12960
```

```
atcctccgat ggaagattac acaacaacgt agctccgtaa ccatatacaa cttttggtgc    13020
aacataaccc tttccagata taccttcagc gaccaaatcg taaacaccag gcagtatctt    13080
agccggaagc ccaagtttga ttgcttctgc aaaaccgtct tttactgttt taaagtcagc    13140
accacttgcc ccgattgtca cataatcttt aacatctgtt tttacattta aaactatgtc    13200
cgctcctttt tctaagtatt tttgatggtt ctcaacagtg ccaaaaaatc tagtttgagc    13260
gacacttgaa gagtcctcaa taacaagata attagcacta gctggtgatg tgacagttgt    13320
attccactga tttaaccca tgttagtaaa gtatttcaat ccgcttttaa tgtcatcaga    13380
ggcaaaaaat gctgcctgag aaatacttgt agtcattatg ttaaaaaagt atgtcgtgtt    13440
tggctctatt ttgataaaga ggtacttacg tacaccgcta tcaatccaaa tcgcattgtc    13500
agacccgtcg ttagcgtgtc ttacaaactc tcctgttaca accttgctaa cacttgatag    13560
taaatttaga cgtgtaacag tatctgatac taaattatta atttctgcca ttttcttatc    13620
caatcctgta aactgctgcc tagttgcttc accggctgtt ttgtagtttt tgccatcgta    13680
accaaacctg atatcaacaa gttcggttgg caaagtgcca tttcctgcag atgcaacaat    13740
gttatttaaa cgttcattag ttgatgatag actagttgta tttgtatcta tttttttatt    13800
tattgttaaa aaatcatcaa tgcttttttga ctcaatgtta tctaatcttg catctaaatt    13860
agattgaccg cctcttgcta aataaatttc gacatgatca cgcaatgcat tatcatacac    13920
tttattcatt ttattttgca agtcaacaat actactgtct tttaatttta aatcacttaa    13980
tatacctgat aacgtcatgc tgacgtcgta gtttggtatc aaatctttta aatcgtagac    14040
agtagcacct tgttctattg aaataattgt agagcggtct gatggaaata tataatcatc    14100
aactttaatt tcaatgtaat aatttccgac tggtacagct ttgctaatgt taaatataac    14160
agacgaatct ataatcgtag atgttgtaga gtagataatt ttattatctg tgcaaagtgt    14220
tattaacgca gtttttgaat taagggaatc aaaataatta ccgtatctat cgattaaatc    14280
aaaagataat tttgaaccaa aatctcsctg ctttatcttt gaccctccga ggtcttgttt    14340 taatttagt gtgttttcta aatacatttta ttccccttta cgatatcctt tggaagcgat    14400
agatagactg gtctgtatct tctagcattt cccaacttcc gcccattaaa ctcgatggat    14460
ttgtattatc tttgctttga taaatagcac caactggtaa aaaaagattt aacaggccgg    14520
aacttttatc agaccaaatg taatcggacg gattatttga ttgcttgata ccaacgtagt    14580
aaccctcgaa tcgtttattt gcatcagtaa gactaaaacc agatgaacca tctatagagt    14640
cagaccatgc cttccacgac gttgaacctg atgctccatc ggaaacattt gaaaatgtta    14700
cttgcctggt tgataccaaa aaattattaa tataagcttc aacaactata gacaatgttg    14760
ttgagaaatc agaactatta acaacatatg tattaccatt tgatagtaaa ttttcattgt    14820
ttttaaactg aaaagttgca ttaaacttttt tgtttgattt ccacagttct gctgtcaata    14880
cacttcttcc agtgctattt ttaaacgtag taccgttgtc agtgattaat cttaagtcgt    14940
atggtttagc ttcttctgtc atatcgttca tacggtcaat taagattgat gatgttttgt    15000
tttcgagggc tttgtagtta tcaaaaacag ttttatttttg atttggctct gtaaacgata    15060
tgtgttgttc gctgaccctc gcttctaatg tcaggttagg actgtactct ttatcgctga    15120
ttttaactgt gtcaccaaca tcaagattag ctacatatcc aacaacttcg taggtaatcg    15180
ccggataagc gttttttcgt agcgttgcta atgcagttga tataagtact tcctctgcat    15240
cagtttggac ttcaatgtct tttctaatcc agttatcgtc tgtctctctt ccactaaaag    15300
```

```
ctgatggata gaggccttta gaaattggtg catataacat cccatttttt aaataaaatt    15360
caacatcgcc tttatcattt ttccactctc tgtagagagt gtctgagata gtgatagtct    15420
tctcttcgct cgtggttgag gtctctgttg tactgtcagg tgtaggctct gttatgccat    15480
cgatgcgttt tccttggacg atttcaggtg gataacaaac agtttggaca acgcctaaat    15540
aagcgctagc agagtagtta cgttcttcaa cgtattgatg ccctgcgaag ttttgctcta    15600
aaacggttag tgtatcgcca gagatagctt taataactac agtatgcccc caaccactag    15660
tatagactgg accacctgcg tttgctttga tgtttgcaat cgcacccggt atcaaatcag    15720
caacacttcg aggtactatt gatttccaac cgaactgccc ccagttgtaa tctgtgccga    15780
tttgtgatgc tgccatacca ccaccaacaa gacctcttaa actagtgaca cctccaccaa    15840
gacctgggcc gtctaatgcg tttgcatacc acgctgataa tgcgtaacac tgaccactcc    15900
caaccaatct accttttaaa gtcgatgctt gataaagtac ggattttgtt ttacttgcaa    15960
tctgagtaac tggtgcttgt ccaactgttc ccatggattt aaattgattg tcaatattat    16020
ccatagcatt gttattattg cgattaatgc cagacctaat atctcgcatt aacggtgcat    16080
aatgagcata tccagctgca gcataatcat atgttgcacc accaactcta aacagaccct    16140
ttgtatagtc gtcaatagta tttgcgcctt ttaccttgta gatgccttgc tctgccaaaa    16200
ggtaggtgta atctttaaag taatcagata tattagcaaa gtgcatataa taaccgccct    16260
ctgatgatgg tctcgaacta ccttgcgtaa ctttaacacc tgatgccctt gttgttgagc    16320
ctgtccacgt taaaccaccc cagttattat cgacacgagc aacgttggaa ttcccccaaa    16380
atgactctaa gtacagttgg ctaaatacac ctgacggtaa caacttatgt tgtgtacaca    16440
gacttaatat ctccccaaca atagctggtg gaatgttatg cccagcgtaa ttaagattac    16500
ctcctgacca agtaactgtt ccaagtttag ccgaaccttg cttgacagtc gttgtggttg    16560
ttgtcactgt agctttgcct cgcgggtaaa ctgcattaaa tacaccagtc ttatcaatct    16620
tacgtctaac accatcgata ttttttgccat acgataaaat gacatcatca cggcgttttc    16680
ctacaccttg attcttaccg tcattttttt tgtaaatatt cattacgaaa gatttcaaac    16740
tagagtcgct tttaagattt gtcacaaatt cgatttctgc atcaaaatta ttagcaatgg    16800
ataataagcg tttgagatta gtatcttggc cagtccattc tatagttcgt ttttggtcag    16860
ctacctcatt aactccaatt gttatcgcac cgtattttaa aacaccaaat aaattgcaat    16920
aatcaacaaa tgacaattga tttgcagact tataaggtcc tgcgtactcg tttagcagtt    16980
cgagattcag atttcgcag taacaatgga tttctgtgtc tgtttcgtca gttgtcataa    17040
cattaaacaa ataagtgcgt ccgttatatt taaacgaaac aaaagacctc tctgttaacg    17100
tcagataggc cttttcttta actgtgtctg atttgatacc ttttttgtaa acggtaaact    17160
caaaagtcga gttagctgtt ttcaggtatt gcgaaaactt gtcgttgtaa taattcaagg    17220
tatcttgctt gtcattgtcg ataaaagcta ccttttcaag acctgcattg tgtattgtaa    17280
taagcattat agatacctt cttcaaattt aatttcaact tgcggttttg attctaccca    17340
ctgcgaagtg tacaactcta tgtttgtttt gcctggaggg attttgataa agtctgggat    17400
atcaataatc tcgcttatct ttttaattcc atcgattgta aaagtgtcat tttcgctatt    17460
gataacaact tcgcttcctg cactaaatct atttggcaca tcttcaattg attcgataaa    17520
atctttacga taatagagac tgtctaagta caagtgtgca accattggat tgctaccaat    17580
agagccaata atgacgtgta tttttttaga tttacggcct ttgattcctt tagctactaa    17640
cgggattgat gacccttccc atgcaacgga taacttgtca tcatttcgtt tgatttcggc    17700
```

```
aaatccgtta actgtattaa atggattgtc gctagactca ttagtccctt taaaagtaaa    17760
tcgctttaaa acttcaaagc tgccgttacc gtcgctggcc aaaatgttgt actcacaatc    17820
tatacctgga gacctcttat aagtttcgac accatataaa aattggtcat tttcgtcaga    17880
tacggttact tggataaaac catattgatt aaaaccatca ttccacatcg tttgtctcca    17940
ccaaatgcaa tcgttcaacg agcctgcctc tccttttgag tcagcaggta ttggccaagt    18000
gagacttcct ccgttataac cagtcatatt tctatatgtt gttttgatgt gcttttatc    18060
ccacaagtca ataacagaca atgtgttttt aagtgttagc aaattagtat tattgatagc    18120
tacgttttt tgagcatcat taaacccttg gacaattttg gcatcacgat aatcaagtaa    18180
tatttcagat ttattgacag tttcacggtc tgtttcttct cgactacctg cctcaaatat    18240
ccctgtttgg tttactaatc cgagataacc attttccgtt ccgtgtttga tagtgataat    18300
ggggaatgca tcagtatttc cgttgttgac aacttcaatt acctgcttat cttcttttc    18360
aacaattttt ctagctcttc tgtgagcaac tgatctagca actccatcag gtacaagaaa    18420
tgtgatagtg ccataagaac gtttgattga tgcttcttgc atttgaattt catcaacaac    18480
taaagccaga taatatttat ccggctcgtc actaaacaat aatttttag cttcagattg    18540
attaaaaatc gaagctaatt gatgcttaac tgaatttcta tctctagtcc aaattgaaaa    18600
agaaacagtt attttttag agtctatttt atatctttga attacagagc ctataaacgg    18660
agatgtgtta gtagtaacaa ccctgttatt accaacacct ctcttaatgt cgtgaatctc    18720
aataagtgac gacaaatcaa actcgttgta atttattgtt acttttccta tactaactca    18780
cctctcaatc ttttttgtct gaaattttct gtttcgttaa attcttgaac taatcttcct    18840
acttttgtt tatcaagata aacgctgcct tcgttattac ttcttgtatt gttacttttt    18900
aacattagta gaatttcgtt caaaaccctg acgacatttg agttatcata taaacagac    18960
gatgacgatt gatcacttga cttagaaata gttctaatta aatttgagtt ttcagggata    19020
ccaacaccac tggcgtatct agggattcct atatttttca tgaaatctct tgtcatacta    19080
gctttcataa ctttagtacc tctaggaagt ggcaagataa catctcttcc ctctggtata    19140
aacgattgcc cattcggaag tgtgattaat tctttataaa gtggtccact ttggtcatta    19200
accattgcta aaccgccttt atggaaatta gttccagtcg catgcttagt tatttcttta    19260
taaatatttt tgaaaataga ggtgatagtt acagtcttgt ctttaactct cgagatgttg    19320
ccgactgcgt tgtcgacatc ttttttagtc atatcttttg caattaattt cttttcttcc    19380
ggtgtcatac tatcccaaga ttttaaaaca ccagttgcta attcttttt attgataaaa    19440
tcttggttgt tacctaaaat ctgtttaact ttttcaggca tcgaatccca aatagctaag    19500
ttagatttgc tatctgcaat tgcttgtaat ccttgatgat tgccaataat tagttttttc    19560
tctttcggag ttaacgtttc ccatttcct gtctcttgaa gcacctctgc cattgtcaat    19620
cttgcattag ttgacaagtt agcgttcttg gcaatgaact taaggttttc ccaaccgccc    19680
tcagcttgta aagcttttg aatttcttct ttgacgttgg ttttcagttt tccagttttt    19740
tgattccaaa ccataccatt ccattgtgag tttgctagct tagttcttc gcttgctttt    19800
tttgtggtac ttgcccacat tgaattattg gcttgaattt tagaagacgc tttagtcgtt    19860
ttttccatta actgttcgta tgataagcca agttcttcca tttgctttt aacagagtta    19920
attacccctt gttgcgtctc aggatctaac cctttttaatt gattattgag aagtttcttt    19980
tgaatagttg cgtacttctc accataagca tctaacttag cttgatggct agcttcaagt    20040
```

```
tttcctaact tgtcatggat ttctttcttc gcctttacag cttttcatc atcgccttt      20100
atagacttat acatttcctg aagattgtct ttacgttttt tgtaagtttt attttcatct   20160
tcaatccatt tttgagtagt cttcaaagct tcacttaact gcgaattatt tagaccttgt   20220
aagtcgccgt tcaaagcttt tgtaattgcc ttacgctctt tagcagagaa gttcattaac   20280
gacaactgcg tatcaattaa ttcgttctga ttttgtaaaa caattgcttt tcttcagct    20340
gttaaatctc tatgttgttg acttgcgttc tgataaatgc taataacctc atcagacatt   20400
tgttgagcat tcgcaacagt ctgttgactt gattgtttga tttcattcat cgtttcttca   20460
ctcaacccaa gagcttctgc aacattaagt ttttacgta agtctttatt ttgaagtttt    20520
tcaatttcag taacaagacc ttgaaaagca gttttaacat tattaacatc attaactgaa   20580
tcacttccaa atgtagacaa agctttatta gtttcatcaa ctttattttt aaacctcgat   20640
aactcgttag cttcaacttc gttaacttta gttccccaca attgagtccg ttcgtgagct   20700
tctaaagctt taccaccaaa gtacgccagt aacccagcac ctgctaacaa tccaactgct   20760
aaagctccgc cgggcgttaa taaactagcc aacaagccac cttgtgttgc caatccactt   20820
actccagtag ttgcaactgt tgcagacgct ccgactgttt caattgctgt agatgttgct   20880
tttagttttg ctaatttgct aaaccaacca atacagtgc tagatgctcc agttactgta    20940
cctaatgctt tgaaaactgg ataggcaccg gccgttatca aacctaaatt aattaataat   21000
ttttgtgtag ctggatcagc ttctgaaaat ttattaacta agtctgtcac ttttcaatt    21060
atcggtgtaa gtgttggtag taacttctga ccaacagtaa tacttaatac ttctaatgat   21120
gatttaaact ggtcaacttt gcttttgat gaaccagaca tttccttggc taaatctgag   21180
gtataacctt ttgcgttttc agtttctttt gagagatttt taagtgcatc tccgccttga   21240
tcaactaaaa tattcattgc tgactgcgct tctacaccaa acgcttgcga tattaacgct   21300
gccttttgag cgcctgtcat atcttttgtt gatgacttga ttttatctaa tacgtctggt   21360
agtttaatag cccctgttct aaactgttca gatgtaaaac caagtttatt aaacgcaact   21420
tcattttctt ttgcagggtc aagtaattta cttaaagcac cacgtaaagc agtacccgct   21480
ttttgacctt cgatacctgc attcgataat agaccaattg cagatgctgt tgtttctaca   21540
ctcataccaa cagattttgc gactggacct acatattgca ttgcaagtcc tagatcttca   21600
aaccctgatg ctgtttttatt ggccacaaat gacagtgagt cagtaactct actagtatct  21660
ttggcttcaa gtccaaactg ttgtaacgta cttgttgaca cgttcataac cgtgttaaaa   21720
tcatctccag atgctttagc agcatctaag atggccggca ttgcgtccat cgtttgatta   21780
aacgtgaaac cttttttaat aacttcttgc ataccatcat ttatggcagt tgtagagata   21840
ccgtattgtt ttgcccaacc tttagaagca tcacccattt ttttggtttg tgcattaat   21900
tgttctactg aacttgttgt gtctctaagt aatgctcttg ttgtttgcat ttggccatcg   21960
aaatcaactg cttttttagc tgcataagca agccctgctc cagttgctaa tgatgctgtc   22020
ttagttgctt cagcaaactt attaaacaag ttactagttg ttcttaattt tccagataac   22080
tcgtctaatt ctttagatgt tcttccccaa aaactatttt cagcgtttac tcttttaaa    22140
gcactggaaa cttgattaag ttcatttttcc attgcattta gctggcgtt ctcacgctca   22200
atttgtactg ctgccgcttc ccacttcgca gtgcctggct ctagctcatc atacttagct   22260
tttaactgtg tcaaaacttt cttttgagca actatttgct gttcaattga tttatatttt   22320
gtaccaagta atgacaagtt atttccgtta ccttttaggg cactgtctaa tgctcttgtc   22380
tcagctttaa aataattgac ttctcgcttt gcgctttgaa gttttggtga aagtttgta    22440
```

```
gtatcaagtc ctaactcgat aaacatactc cctaatggtg ttccacttga catattccct   22500
cctttcactt aaaataaaa aggcacaatt aagtgccttg catttgtctg acaaaatcac    22560
ctagaggtat aatatcttct tggatttcat tatcttcctc atcatggcca atgacagcca   22620
tcaggtctct ccagtccgtt tccatgacat cctttactga taatccataa tcagacttga   22680
taatacttct tgagaattca tcaaattttt ttaatgcttt tttagcactt attctgtttc   22740 cttttttcg gcttcaccgc caatcaattc aacaaagaca tcggctatta aattatttat    22800
ttctttcata ttcattccgt catacatctt gtcgatagtc aacccttcaa aaagtgaaga   22860
aataaagtta agctgaatgt caagagcttc tgtttctgat aattgttttt cttcaatatc   22920
tgcttgcatt gctagatatt cacggtattt acgagctgga agaaagtcat tttcataaac   22980
aaccttctct cttttctcgt tacgtacttt aacctctaat tttgccatct attaagctcc   23040
tactgtcata tcaagcaagc ttgctaaagc tttagcattt gtacctgtac catttgcttc   23100
tgtatcaata cccataccga catattgacc tttagcatct cctgttgttc ccggttgtgc   23160
taagaacaca agttttttgcg aatcaaggcc ctctttctta ctgtcttgag tttttagttc   23220
aaggtcttct ttagagaacg ttcctttaaa gaaaccgaag taagcatttc cttctgtatc   23280
tggtgcttcg agcaaaatag atacttctgg agcttctgtg tcctctccga tgaatgttag   23340
accagttgct gttgttcctg atttgtaacc aaaaattact ttttggacag ccataggaat   23400
gtcaattaat tcaaactcag ctttcacttc accaacacca cgacgtgagg tatagtaggc   23460
aatatcagaa ccgtaagtct gaataggatc agcagctaaa ccactaattt tagcagtttt   23520
ggtcgcacct tttcctgact taccttcaat tacaaatttc ttttcatttt gtcctaaaac   23580
ttggatcgtc atacgtttaa atccgattgg ttgcattaat tttctccttt aatattcttc   23640
ataaattttg ctgaaacctc tataggtcct agcatctcta tatctatttg tattgttttc   23700
aaatccctca agacctgaat ctgattgaaa aaaacctatt gttgacaata gaccttcaat   23760
cttatgttgc aattctttgc attccattct tgagatactt caacctcaa tttgatacaa    23820 aaatttttta gataatgggg catcagaacc aaaatcttgt tgttgaggtg gagtaattgg   23880
aataataaca atactagtgg aatcatctga cagactttct ggccttgcaa aagacttaat   23940
cttgacttgt cttatcgttt catttgtctt taacagatca gcaatttcca tcatcatatc   24000
tctgaccatt atattttaaa ttctcctttc aatttttctt gtatccttg aggataaact    24060 ccttcgaggg aatcagaata gcgtctgata acaccgacac cacgcttatt cttcttccaa   24120
ccgtactcca tttcttgtaa atggactaat ctgtaccgtg gcgctgtaaa gccaagtttt   24180
attttaggga ttccttcgct acgttttacg ccagatactg ctacactttc cattgtcata   24240
ccagttcttt gataaactga tactgcttct ttaaatgtcg gttcaaactc tttttccgact  24300 tcctttagcg ttttgttcac tgctctgtta actttcgcag agcctaattc tttttccata   24360
ttcgctaata gttcatcgat tccgtttagt tcagctccca tatcagtcac tgctacgat    24420 tataataaag tcgtcatcta caaaatcagg tctaatatca actatcccta gcttttttaga  24480 ctggactctt ttatctaaaa tgtctacttt gtggtcatta gatggataat aagcagagta   24540
tggactccgc attttatag tgtattgtgc tttaactcct ctatcacttg caatagtaat    24600
atccttggaa cttggattgt aaacttctgc tagtgttcta aaaagttcgt taagtttaat   24660
atcacggcca tctagtgagt catctgtagt tgctgaataa aatacgactg gtgttttaa    24720 atcaccgtta tttgtttttt gtttcatcat cttttacttc ttcaataaaa ttcggaagat   24780
```

```
tttcgtcgat ttctttaaag cgtgtttttg taacttcaaa ttcatctcca atctcacgga    24840
ttttatcttc tttcaaatct ttaaaacgta gaagtgtttt tactttcata ttctttctcc    24900
agcccgtaca tagctaatct agctatctca ttttttaaacg aatcataaaa caactcgaga   24960
ctgtcattat aaacatatct cgagcgttcc ataattaatt ctttccctga ttcaatagtc    25020
attaggtcaa agcctaataa gctatttaaa gcgtcttctg agctatttaa aatgttattg    25080
atgttttcgt catctacatc atgaaacact ctcatacgct cttaaatcg ctttaagagt     25140 gcattatttt ccataggcta ttaaacttct ggcaaagctt cagggactgt tagtgtccaa    25200
acagctgctg cacgttcatc ttttgcacgt ccgtaagcaa attgtttagc tgtaaacaaa    25260
tctaggtctt cgatagcaaa tgtttctgtg tatttgcgca actcaatacc gcctgcgata    25320
tatgcatcgt aacgaccttt aacaaaagta gtaacttgtt tcgcagtttg atgtacagat    25380
tcgattaatg ttacattaaa cggcattgca gtcacaaata caccgtttgc gtttaatgta    25440
gtatattgtt ttttgatatc ccatgcgtct actggattaa caaccattac gatgttacct    25500
tcaacgttaa ctggtgtttt accatcttct tttacagagt gatgtttgtg tactccagtt    25560
aattctttaa cagttgttgg tgcatcttta aatgtaagca cacctttgg ttttttagct     25620 tcataagttg cttttttcgcc aacgacatga ccactcaatg tgcgtgatag tccgattggt   25680
ttgctatttc catcaccatt taaaaatgct tcttccaagg ctactgcaaa cgcttcgtta    25740
atttgtgttg acacaaaatt aagtaaccaa gcagggccaa attttactgc atcttttggg    25800
ataactacaa atgccgtaag tttgtgttgg attgctttac tagagctaaa tgcagcagtt    25860
aactgacctt tgatttctcc gtagagttct ccccattctg ctttacctt agattcagag     25920 tcaataaact tcatgaagcc ccatattctt caatccgata acttcaagca atggatgtgc    25980
tgtaactaaa tcttcaaaaa tgcgatcaac agtttcttct gggataagtt ctgtaatacc    26040
tgttggagct gttttcacga tttcattaaa gaatttgcgc tcacgagcgg tcatcttcat    26100
ttcttctggt gtaagtgcaa tagcagactc aacttccgaa gaagctacct tcttagattc    26160
ttcaaacata gcttctaaca tttcgccgta tagttcagat tgcacttctt gaggttcatt    26220
cgcttgtact gcgttcaaaa attttttcacg gattgtgtta aattcatttg ataatttcat   26280 tgtcatatt taaatttctc cttttaatta aaacaaaagc cccaaatcct tttgacactt     26340
cttttcttgt ttagttttc tacttcttca tttttgttg attgttatac tcactaactg      26400
caattgctaa ctcagcaatg tctggttctt tttgattaac attaatagca ttagccagtt    26460
ttgagataac ttcgctaggt actacgttct cgatccctgc tactaattgt ggcgcttgct    26520
taatttcttc tgcaaacatt tctttatctg caaaaccttt atcaacagct tgttgagcag    26580
tgaaccaagt ttcttttgccc atcaagtcta gtaattcagt catttctaaa cctgtcttat   26640
tgacataggc attagcaatt gatgtgttgt aattttctag tacgccagct tcgtgtaaca    26700 tttgttatg atcaccactt accgtagttg atacattatg tatcatgatt tgagcagttg     26760
gactaatttc aaccgtatca ccagccatgg caatcaccga tgctgcactt gctgcaatgc    26820
ctacaatctt aactgttaaa ttcccttgat aagattttaa agcagtgtaa atttcactcc    26880
ctgcgtatac atctccgcca ccagaattta ataacttc cacgtcgcta ttatcttgcg      26940
gtaagataat atcttttggc gcagtagctg gcatgtctag ccaatcataa aaccaacggt    27000
cgccgtctga tacgatcggt cctttaattt gtatctgtgt catttagatt ctcacctcct    27060
ttcccatatt caacatagtt tttagtcata ataaatttct ctccatcttc gatatcatca    27120
aacccaaatt cgttacgtac ttcatttcgg ttaaatgtac cactggcaat caacttatca    27180
```

```
atgtttgaag cacactcaat aatgtttatg tgactaagac ctacaatagt aatgaacgta    27240 ccttttcat attcgtcttt actaagtagt tttgcattta gttcgtcttc cacttttta     27300 aataaaggtt gcatacaata aataacaagt gcttttgcg agctgtcaag ggttgccata    27360
tcaccatgca atacaacagc tggaatacct aagatatctg ctatctcatc atcaaactgt   27420
cgtctgattg ttttaacatc atctatagat atgtttgatg tgccagttgt gtttgttaac   27480
tcgttatact caagtccgtc tactgttggg acgattgcaa cagatcgagt tgaaaaagca   27540
ttaaataatt tatcagaata gctttgcatc aattctcttc ttttatcaac catctgctga   27600
gaacctttaa attctaatgt cccacggatt tggttatttc gttggattgt ttcaatcatc   27660
cgttgatgca acttttcata gtcagcaaaa agaccatcaa tataatttga tagtctatta   27720
ttgttatatt gtaagtaaac aacttcactc attttgaacg ttcgcttaaa tgtgtaatct   27780
ttgatagtga cttgttggaa caaatcttca taaactgcat attcgatatg gtcaaagcta   27840
tctgcaatca gtaactggtc atcatctgac aacacaacta atacttcatt gtcggttata   27900
agtttataga taaatctttg ccaaaaccgt gacgatgatt cattttgtt tggtttgaca    27960 ttgagcatgt aggaccatgt tttttatca gagttcaaaa atttaaagtc agagttagaa    28020
aatatcctag ctaaaaattc agctgattta tcaattgcca gattctttaa gtagagattt   28080
tgatattcta caaataactc atcaatatta tagctacttt ctggaattgt tccagtttta   28140
aagacactac caaagaaatc aaatagtttc attcatttcc tccttctttt agattccatg   28200
ataaccctgt cggttgggag atgacgagat cacttccttt cagttaccaa tatttttaa    28260 attcaccaac tttttctaaa cctccatcaa aaatttttata aatacattca ttaaaattta  28320
tataagtgta tccattttta taagcaatat ttctggcttc tgaaattgta tgaccaggat   28380
ctatctcata gattatttct gctctaccaa cttgcttttt acgtttacaa ttattgatat   28440
taaagttaat acctaaatta ttaagtttat ccagtgcttc ttttacgtca tcaattgcct   28500
tttggacttc attgatattt tcaatttcta aattcaggaa catagttccg gttgattcta   28560
atttcactac tttccctcct aaaaatccca atcagcaatg ctttctaaaa actctccaac   28620
attgctatct tgtatgcttt cctttttata aagcgcagat ataaaagcat gaaatccatc   28680
tgtctttctt cttactggtt cttctcttcaa aaatcgttta ttgcctgatg catcttcttt   28740
aacaaaagtg ttgtccgtat accacaacat cattctgtca tcatctaaaa agataaagcg   28800
ttcattagca aatccatctt caataatcgg tgcgacttta ctttgaatcg ctccagggtt   28860
tcttaaaaat tcatattcaa aaccttcttc ttcaagcaat ggttttaata agtccatacg   28920
gaatccatca gcacagacaa tttcgataaa atgatcgttt ctccactcta ctaacttatt   28980
aattagcagt cttgggtcta tgctatctcc atcaactaag gttaacagac catttctctc   29040
ccattcctca ataggcgctt ttaatttaaa ggctttaaaa aattcacgtc taacaaacga   29100
gtgttgcttc caaataaaat catcgccatt cttaaataac aatccaacag atgcaaaatc   29160
tcggatactt gcgtagtcga atccagctac acaagaccta ccttttaagt ctatttcagg   29220
ctcccgtaat gtagcaagta gttttttcacg actggtaaca tcttttttcaa ggtccgcttc  29280 tggtaagttc atgcgctttg tcataaactc ttgtcttccg cttggctcaa gttctaaatc   29340
gtcatagtct gattttgtag tagtccaaag ccttttggca tatgacgtat cttcatcaag   29400
cattggatta gctttcggcc agttcttgaa atcatcaact tcctctgcat tatctaattt   29460
gcagatgaat gggaacattc ggaagtcgtc tacttctcct cttaatatcc gactagcttt   29520
```

```
ttcaatcgtt ttgtcataaa acccttcacg cacataacca ttcgtaccat taaaaaatgt  29580
tcttacatga gcaatctttc caaggcctga tttctgcacc ttaacaattc tgtcatcttc  29640
aaattggtga atttcatcaa attcaagaca accatctcgg gcagagtcca ttgttttggg  29700
gttatttgtt ctaaaagaaa agacggaatt attcttccgt ccgacaatag ccattttgt   29760 taagtagtaa tgattttcta atccccttgc ttggattgtt tcatatactt cttcaaatga  29820
tactttcccc tgttttcac  tgttggcagt aattgtgaca tcataatttt taataggata  29880
taatgggctt gtaaaaaacg catccctagt cgacataaaa ccattcttac cacctccacg  29940
agcaagtgtc aaaaggtatt cattaaaatg tggttcgcca tcttcttttc taaataaaaa  30000
aatgaatggt gtaataaatt tctgatatgc tgccaaagga aagaaattct tttcagcaaa  30060
cctcacatat ttatctatta aatcattgtc aaaatacaaa tcatctcgag tgagtatctt  30120
ttctctgatg attttaacta attgttttcg ctctttgtta taaacaatta aatcgttatc  30180
aatcttatgt gcatattctt caaacagtgg atgtgaaatc aaataagatc accaccatcc  30240
gagtcatgtt tcgtctgcac attaaattca aaagattttt caattgataa tatctgcgca  30300
ttaatcttag ctttttcttg aagagcggga ttagtcttta gaaacacttg actgccattt  30360
attgtctcaa ctaatagccc ttgttcttta atatatttat ccagtttata aaacatttca  30420
attaagttta gataacgctc aacctttct  aattgcattt ggtcatcagc gttaatcttt  30480
gataataact cttttttag cttctgttgt gtgtatccca cagacacccc ccttcacgt   30540 aaaaatactt aaatatttgg acagtcgacc cttcccaccg gtttcaaacg ttcggttttt  30600
actgattatt tttaagtggg gggtatctat ccgaaccact cgtcagaacg ataatttgtt  30660
tctttctcaa tcttttttctt tttataatta aaacgtttgt gtcttttgtt atgacagtct  30720
ttgcacagag tcctaaggtt atcaatgtcc aatgcaaact caggatagaa ctctaactct  30780
ttgatatggt caacctctaa gttagtcttg gttaccttac cttctaactt acaccactga  30840
cattcttcgt tatctcttcc aattgcttca agtctcaatg ctcgccactc ttgtaagttg  30900
tagaatgtac tatgtcttgt tgccttagtc gatatgtcaa tctgcataat acctccataa  30960
taaaaagcca ctcaatgagt gactaagtaa gcgtgcgagc ggactcgaac cgccacgcct  31020
caatgttgaa ctatcaacat aataaggaat cgaaccttat tgccaagaca cgctttatag  31080
gaacagtcgg aatcgaaccg acacatcgaa gtggtctgct tcaaacgtgt ccacctctag  31140
tagttttcca atcttggctc atgttcctat tgagatagca ggattcgaac ctgcgacgct  31200
tccattattt atctcaactg atattgtaag tttggtttat atgttgttgt ttactacttt  31260
gtagctatta gttaatttat accgcttctt acaattatct atgatactat aatactaaat  31320
taaatagtat ttgtgagtaa tagttagtca attataatac tatagtagta ctatttagta  31380
aatcattgag gttttctatc gctttccttt tgattgtata gtatgtgttg cggttcattt  31440
ccaatctatc tattgcttcg tcgtaagttt ggcaattgac gaatgtagtt accaacacat  31500
gtctttgagt tatgtcaggt agttgcataa ccatttgaat gatattacct tttcgtctgt  31560
caagctctcc aatctgttca gcataatact caccttaat  gatgttgtta atattcttgt  31620
cagtctgtga ttgcttaatc cctccttgga ctttcatgtc agaccactgt ggactagaca  31680
acacagattg actagtagtc atatctcttt caagctcttt aattaatttt ggtattaccc  31740
ttaattcttt taacaacata tcagcttttg tctgattccg ccccattcca agtctcctta  31800
tggtataata tagttacgaa ctaataccaa ggcgctcatt ctgttgggcg ctttttgttg  31860
tcttatcgga gtagctatac ctctttcctt tttttatttc ggacaggcac acgatccgca  31920
```

-continued

```
ttgaaattct cacagtgcct tgaataataa cagatgaccg ataatctgcg ttagaatgtg    31980
tacttatatg taaggagcct ttcttatttt tattattttt tcggtctatg ccacatggcc    32040
cgattagagg tcaagtggtt atgtccgcca aaatcaataa ctattgcttt tgacttgtct    32100
ttgcagccaa cgatcatgcc gtaacgatta atatgctctg ccccagtatc attaccataa    32160
tacttagtta tttttaaaac tcctcaaaat aaaatttacc tgaaaatggc ctgatttgaa    32220
cgatgccata atctatacct agcctactga taaaaggctt agtgatacgc tcatgcaaag    32280
tcatcatttg ctgtctaaaa acttctaggg tcattgcgtt tttataataa ttgcacgatt    32340
ggcaagcagg catataattg tccatagtat cctcaccgcc aaaaacaaaa ggctctaagt    32400
ggtcaactct tagcgttttg atgtctaata ttttaccgca ataggcacaa tgacaatcgt    32460
atttttccaa gacaagttgc ctagtctttt tacttatgga tttacgtttc acctcaactc    32520
ctccaaacta atccatttaa actgcgggaa ttgttctgct tcttttttgag tgcatttgtg    32580
accataaaaa tttacttcac atgggctgtt agttgaactt acagttaatt tcttgttatg    32640
acaatctatg ttttcataac ataaataatt aaacttccaa ctcggttctg gcacatcaac    32700
tagtaacaca cctaattttt ctgtcatttt tccacgcttt ctagcaactc actgttttga    32760
tatacgttgc cgatgatttc aatagtttca caaccatctt cggttggact aagataccaa    32820
aattccccat ctttccacgc tggacataat aaccacagtc catcaattct tctttttatt    32880
tcaaacgttc cttttacacc ttgcgaccaa gctatcacga catcccttc gaaaacatca     32940
ttacctttt tatcaagtag tcctgtagat tgcattggtt cgctaaacat gctgtcatct    33000
gtacttaacg ccataaacaa ctctgataat tcatcgtatc catcagctat ccacatttca    33060
cgactttcaa aatcgtatac tctaacttt ttcatcactc cacctccttc gcccactgcc     33120
acaaaaaatc aaaatcctgt ttgatttcgg attcggtgag gtgcagatat tttggtttgt    33180
taatgttagg gtttaacata tcaagaatta accgccctgt actttgttgt ttaaacaaca    33240
ctagttttcc gcctgcgcta tttggatta                                      33269
```

STREPTOCOCCUS INIAE BACTERIOPHAGE STR-INP-1 AND USE OF THE SAME FOR INHIBITING THE PROLIFERATION OF STREPTOCOCCUS INIAE

CROSS-REFERENCE TO RELATED APPLICATIONS

This application is a U.S. National Phase Application of International Application No. PCT/KR2016/010954, filed Sep. 30, 2016, which claims priority to Korean Application No. 10-2015-0141281, filed Oct. 8, 2015, each of which are hereby incorporated by reference in their entirety.

REFERENCE TO SEQUENCE LISTING

The Sequence Listing submitted Apr. 13, 2018 as a text file named "08162_0037U1_Revised_Sequence_Listing.txt," created on Apr. 12, 2018, and having a size of 43,748 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Streptococcus iniae* cells, and a method for preventing and treating the infections of *Streptococcus iniae* using a composition comprising the bacteriophage as an active ingredient. More particularly, the present invention relates to a Siphoviridae bacteriophage Str-INP-1 (Accession NO: KCTC 12687BP) that is isolated from the nature and can kill *Streptococcus iniae* cells specifically, which has a genome represented by the nucleotide sequence of SEQ. ID. NO: 1, and a method for preventing the infections of *Streptococcus iniae* and thereafter treating them using the composition comprising said bacteriophage as an active ingredient.

2. Description of the Related Art

*Streptococcus iniae* is known as a causative agent of Streptococcosis and is a Gram-positive coccus belonging to the genus *Streptococcus*. *Streptococcus iniae* is also reported to bring about streptococcosis in farming fish, thus leading to economical damages seriously. Moreover, *Streptococcus iniae* is a beta-hemolytic bacterium causing complete lysis of red blood cells and thus, highly pathogenic to marine and euryhaline fishes as well as fresh-water fish. Precisely, *Streptococcus iniae* is lethal enough to kill approximately 30% to 50% of fish after the outbreak of infection.

*Streptococcus iniae* is isoated as a pathogenic bacterium that infects fresh-water and marine fishes in Korea, japan, America, Israel, Australia etc. Mostly, it is elucidated to give rise to diseases in olive flounder, sweetfish, tilapia, rainbow trout, amberjack, sardine, sea bream and the like.

When being infected with *Streptococcus iniae*, fish is usually floating motionlessly, attaching onto the bottom or rotating in water. Moreover, it often shows apparent exophthalmos, dotted bleeding on inner gill and further reveals congestion in pectoral or ventral fins. In terms of anatomical signs, the infected fish is reported to mostly manifest brain injury, darkened body color, reddening of rostrum, exophthalmos, nebula, congestion of liver, ascites, hernia and the like.

Streptococosis caused by the infection of *Streptococcus iniae* occurs frequently both in adult fish and juvenile fish, regardless of growth state, which thereby results in economical damages a lot. Therefore, it is required to develop a novel procedure for preventing and further, treating the infections of *Streptococcus iniae*. Especially, the safety of sea food is a main social concern and necessarily, environmental-friendly methods are preferred.

The fish aquaculture industry continues to develop rapidly every year, because it makes food resources acquired easily when being insufficient in the wild fish capture. However, as the aquaculture industry develops increasingly, environmental pollution caused by feeds increases around aquafarms. Particularly, a lot of antibiotics included in the feeds are spread widely to rather threaten human health. In the aquafarms of olive flounder and the like, chemotherapeutic antibiotics are utilized in an excessive amount to eradicate bacterial diseases practically. As a consequence, multi-drugs resistant bacterial strains are emerging in a high frequency, which leads to economical losses in the aquafarms. Moreover, such an abuse of antibiotics without any restraint can threaten national health and thereby influence mentally upon nations not to consume fish, which results in weakening overall competition of the fish aquaculture industry. Therefore, it is urgently requested to develop a novel method for preventing bacterial infections and thereafter treating them effectively.

Presently, in order to control the disease outbreak among farming fish, vaccines also have been developed. However, the variety of vaccines cannot catch up with the variety of diseases. In addition, to overcome the multiple diseases broken at the same time, a combined control method to treat them along with the vaccines is required.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria. Due to this cell specificity, the bacteriophage confers antibacterial effects upon target bacteria and excludes commensal bacteria in environmental or internal conditions of fish. Meanwhile, conventional antibiotics affect various kinds of bacteria coincidentally. The use of bacteriophages does not disturb normal microflora either in the intestines of fish, because of killing the target bacteria selectively. Hence, the bacteriophage can be utilized safely and thus lessen the probability of adverse actions, compared to any other antibiotics.

Bacteriophage was first found out by an English bacteriologist Twort in 1915 when he noticed that Micrococcus colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new antibacterial agent that can replace the conventional antibiotics.

Furthermore, the recent regulation of using antibiotics is fortified by the government world-widely. The interest on bacteriophages is increasing more and also industrial applications are increasily achieved.

As demonstrated above, bacteriophages tend to be highly specific for bacteria. The specificity often makes bacteriophages effective upon a part of bacteria, even though belonging to the same kinds. In addition, the effectiveness of bacteriophage is different, depending upon target bacterial strains. Therefore, it is necessary to collect many kinds of bacteriophages that are useful to control specified bacteria efficiently. Hence, in order to develop a use of bacteriophages for coping with *Streptococcus iniae*, a lot of bacteriophages (many kinds of bacteriophages that give an antibacterial action against *Streptococcus iniae*) should be acquired. Furthermore, the resulting bacteriophages need to be screened whether or not superior to others in respects of antibacterial strength and spectrum.

Therefore, the present inventors tried to develop a composition applicable for the prevention or treatment of *Streptococcus iniae* infections by using a bacteriophage that is isolated from the nature and can kill *Streptococcus iniae* cells selectively, and further to establish a method for preventing or treating the infections of *Streptococcus iniae* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used to prevent and treat the infections of *Streptococcus iniae*, leading to the completion of the present invention.

SUMMARY OF THE INVENTION

It is an object of the present invention to provide a Siphoviridae bacteriophage Str-INP-1 (Accession NO: KCTC 12687BP) that is isolated from the nature and can kill *Streptococcus iniae* cells specifically, which has the genome represented by the nucleotide sequence of SEQ. ID. NO: 1.

It is another object of the present invention to provide a composition applicable for the prevention of *Streptococcus iniae* infections, which comprises the bacteriophage Str-INP-1 that can infect and kill *Streptococcus iniae* cells, as an active ingredient and a method for preventing the infections of *Streptococcus iniae* using said composition.

It is another object of the present invention to provide a composition applicable for the treatment of *Streptococcus iniae* infections, which comprises the bacteriophage Str-INP-1 that can infect and kill *Streptococcus iniae* cells, as an active ingredient and a method for treating the infections of *Streptococcus iniae* using said composition.

It is another object of the present invention to provide an immersion agent (medicine bath agent) for preventing and treating the infections of *Streptococcus iniae* using said composition.

It is also an object of the present invention to provide a feed additive effective upon farming by preventing and treating the infections of *Streptococcus iniae* using said composition.

To achieve the above objects, the present invention provides a Siphoviridae bacteriophage Str-INP-1 (Accession NO: KCTC 12687BP) that is isolated from the nature and can kill specifically *Streptococcus iniae* cells, which has the genome represented by the nucleotide sequence of SEQ. ID. NO: 1, and a method for preventing and treating the infections of *Streptococcus iniae* using a composition comprising the bacteriophage as an active ingredient.

The bacteriophage Str-INP-1 has been isolated by the present inventors and then deposited at Korean Collection for Type Cultures, Korea Research Institute of Bioscience and Biotechnology in Oct. 1, 2014 (Accession NO: KCTC 12687BP).

In addition, the present invention also provides an immersion agent and a feed additive applicable for the prevention or treatment of *Streptococcus iniae* infections, which comprises the bacteriophage Str-INP-1 as an active ingredient.

Since the bacteriophage Str-INP-1 included in the composition of the present invention kills *Streptococcus iniae* cells efficiently, it is regarded effective to prevent or treat streptococosis (infections) caused by *Streptococcus iniae*. Therefore, the composition of the present invention can be utilized for the prevention and treatment of streptococosis caused by *Streptococcus iniae*.

In this description, the term "treatment" or "treat" indicates (i) to suppress the streptococosis caused by *Streptococcus iniae*; and (ii) to relieve the streptococosis caused by *Streptococcus iniae*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Str-INP-1 is included as an active ingredient. At this time, the bacteriophage Str-INP-1 is included at the concentration of $1 \times 10^1$ pfu/ml~$1 \times 10^{30}$ pfu/ml or $1 \times 10^1$ pfu/g~$1 \times 10^{30}$ pfu/g, and preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as an immersion agent or a feed additive according to the purpose of use, but not always limited thereto.

For this purpose, other bacteriophages that can confer an antibacterial activity against other bacterial species can be further comprised in the composition of the present invention in order to improve its effectiveness.

In addition, other kinds of bacteriophages that have an antibacterial activity against *Streptococcus iniae* can be further comprised in the composition of the present invention. Besides, these bacteriophages can be combined properly so as to maximize antibacterial effects, because their antibacterial activities against *Streptococcus iniae* can be differential in respects of antibacterial strength and spectrum.

Advantageous Effect

The method for preventing and treating the infections of *Streptococcus iniae* using this composition comprising the bacteriophage Str-INP-1 as an active ingredient, has the advantage of high specificity for *Streptococcus iniae*, compared with the conventional methods based on the chemical materials including the conventional antibiotics. That means, the composition of the present invention can be used for preventing or treating the infections of *Streptococcus iniae* specifically without affecting normal microflora, and accordingly has fewer side effects. In general, when chemical materials such as antibiotics are used, commensal bacteria are also damaged to weaken immunity in animals with carrying various side effects. In the meantime, the composition of the present invention uses the bacteriophage isolated from the nature as an active ingredient, so that it is very nature-friendly.

Besides, the antibacterial activity of bacteriophages against target bacteria is different, even if belonging to the same species, in respects of antibacterial strength and spectrum (within several *Streptococcus iniae* strains, the antibacterial range of bacteriophages contributing to every strain. Typically, bacteriophages are usually effective upon a part of bacterial strains even in the same species. That is to say, the antibacterial activity of bacteriophage is different depending on bacterial strain in spite of belonging to the same species). Then, the bacteriophage of the present invention can provide antibiotic activity against *Streptococcus iniae* different to that provided by other bacteriophages acting on *Streptococcus iniae*. Therefore, the bacteriophage of the present invention can provide different applicability for fish aquaculture industry.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
FIG. 1 is an electron micrograph showing the morphology of the bacteriophage Str-INP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Streptococcus iniae*

Samples were collected from the nature to screen the bacteriophage capable of killing *Streptococcus iniae*. In the meantime, the *Streptococcus iniae* cells used for the bacteriophage isolation herein were isolated by the present inventors previously and identified to *Streptococcus iniae*.

The isolation procedure of the bacteriophage is described in detail hereinafter. The collected sample was added to the THB (Todd Hewitt Broth) medium (heart infusion, 3.1 g/L; peptone, 20 g/L; dextrose, 2 g/L; sodium chloride, 2 g/L; disodium phosphate, 0.4 g/L; sodium carbonate, 2.5 g/L) inoculated with *Streptococcus iniae* at the ratio of 1/1000, followed by shaking culture at 30° C. for 3~4 hours. Upon completion of the culture, centrifugation was performed at 8,000 rpm for 20 minutes and supernatant was recovered. The recovered supernatant was inoculated with *Streptococcus iniae* at the ratio of 1/1000, followed by shaking culture at 30° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing *Streptococcus iniae* was included therein.

Spot assay was performed as follows; THB medium was inoculated with *Streptococcus iniae* at the ratio of 1/1000, followed by shaking culture at 30° C. for overnight. 3 ml (1.5 of $OD_{600}$) of the culture broth of *Streptococcus iniae* prepared above was spread on the THA (Todd Hewitt Agar; heart infusion, 3.1 g/L; peptone, 20 g/L; dextrose, 2 g/L; sodium chloride, 2 g/L; disodium phosphate, 0.4 g/L; sodium carbonate, 2.5 g/L; agar, 15 g/L) plate. The plate stood in a chamber for about 30 minutes to dry. After drying, 10 μl of the resulting filtrate was spotted directly onto the surface of the *Streptococcus iniae* lawns and dried for about 30 minutes. Following drying, the plate was incubated at 30° C. for a day and then, examined for the formation of clear zone on the surface of the bacterial lawns. If a clear zone was generated where the filtrate was dropped, it is judged that the bacteriophage capable of killing *Streptococcus iniae* should be included in the filtrate. Through the above procedure, the filtrate containing the bacteriophage having the killing ability of *Streptococcus iniae* can be obtained.

After that, the bacteriophage was isolated from the filtrate confirmed above to have the bacteriophage capable of killing *Streptococcus iniae*. The conventional plaque assay was used for the isolation of pure bacteriophage. In detail, a plaque formed in the course of the plaque assay was picked up by using a sterilized tip, which was then added to the culture solution of *Streptococcus iniae*, followed by culturing at 30° C. for 4~5 hours. Upon completion of the culture, centrifugation was performed at 8,000 rpm for 20 minutes to obtain supernatant. The recovered supernatant was inoculated with *Streptococcus iniae* culture at the ratio of 1/50, followed by culturing at 30° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Siphoviridae.

The solution containing the pure bacteriophage confirmed above proceeded to purification. The culture broth of *Streptococcus iniae* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Str-INP-1 and then deposited at Korean Collection for Type Cultures, Korea Research Institute of Bioscience and Biotechnology in Oct. 1, 2014 (Accession NO: KCTC 12687BP).

Example 2: Separation and Sequence Analysis of the Bacteriophage Str-INP-1 Genome The genome of the bacteriophage Str-INP-1 was separated as follows. The genome was separated from the bacteriophage suspension obtained in Example 1. First, in order to eliminate DNA and RNA of *Streptococcus iniae* cells included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Str-INP-1 genome.

The nucleotide sequence of the bacteriophage Str-INP-1 genome obtained above was determined by Next Generation Sequencing analysis using Roche 454 GS Junior device from Chun Lab. Ltd. As a result, it is suggested that the final genome of bacteriophage Str-INP-1 has 33,269 bp of size and the nucleotide sequence of the whole genome has SEQ. ID. NO: 1.

Similarity of the genomic sequence of the bacteriophage Str-INP-1 obtained above with the previously reported bacteriophage genome sequences was investigated by using BLAST on Web (http://www.ncbi.nlm.nih.gov/BLAST/). From the BLAST result, it was difficult to find bacteriophage sequences having more than 50% of sequence homology with this bacteriophage sequence.

Based upon this result, it is concluded that the bacteriophage Str-INP-1 should be a novel bacteriophage not reported previously. Either, it is referred that when bacteriophages are different in their kind, their antibacterial strength and spectrum become different typically. As a consequence, it is confirmed that the bacteriophage Str-INP-1 provides have more remarkable antibacterial activity than any other bacteriophages aforementioned.

Example 3: Investigation of Killing Ability of the Bacteriophage Str-INP-1 Against *Streptococcus iniae*

Figure 2:
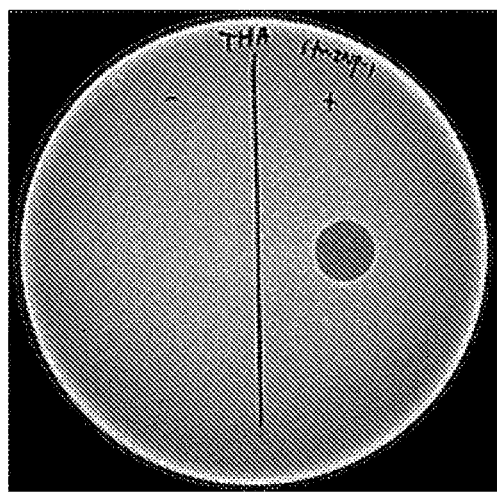
FIG. 2 is a photograph illustrating the capability of the bacteriophage Str-INP-1 to kill *Streptococcus iniae* cells. The clear zone on the dish is the formation of plaque by lysis of target bacteria cells.

The killing ability of the isolated bacteriophage Str-INP-1 against *Streptococcus iniae* was investigated. To do so, the formation of clear zone was observed by the spot assay by the same manner as described in Example 1. The *Streptococcus iniae* used for this investigation were total 43 strains which had been isolated and identified as *Streptococcus iniae* previously by the present inventors. The bacteriophage Str-INP-1 demonstrated the killing ability against 36 strains of *Streptococcus iniae* among these 43 strains used in this experiment. The representative result of the killing ability test is shown in FIG. 2. In the meantime, the activity of the bacteriophage Str-INP-1 to kill *Edwardsiella tarda*, *Vibrio anguillarum*, *Vibrio ichthyoenteri*, *Lactococcus garvieae* and *Streptococcus parauberis* was also investigated respectively. As a result, it is decided that the bacteriophage Str-INP-1 should not have the killing activity against these microorganisms.

Therefore, it is confirmed that the bacteriophage Str-INP-1 has the specific ability to kill *Streptococcus iniae* cells and a broad antibacterial spectrum against *Streptococcus*

*iniae*, suggesting that the bacteriophage Str-INP-1 of the present invention can be used as an active ingredient of the composition for preventing and treating the infections of *Streptococcus iniae*.

Example 4: Preventive Effect of Bacteriophage Str-INP-1 on the Infections of *Streptococcus iniae*

100 μl of the bacteriophage Str-INP-1 solution at $1\times10^8$ pfu/ml was added to a tube containing 9 ml of THB. To another tube containing 9 ml of THB, the same amount of THB was further added. *Streptococcus iniae* culture solution was added to each tube until $OD_{600}$ reached about 0.5. Then, the tubes were transferred to a 30° C. incubator, followed by shaking-culture, during which the growth of *Streptococcus iniae* was observed. As presented in Table 1, the growth of *Streptococcus iniae* was inhibited in the tube adding the bacteriophage Str-INP-1 solution, while the growth of *Streptococcus iniae* was not inhibited in the tube without adding the bacteriophage solution.

TABLE 1

Inhibition of growth of *Streptococcus iniae*

| Treatment | $OD_{600}$ | | |
|---|---|---|---|
| | 0 min. | 60 min. | 120 min. |
| −bacteriophage solution | 0.498 | 0.982 | 1.564 |
| +bacteriophage solution | 0.498 | 0.295 | 0.142 |

The above results indicate that the bacteriophage Str-INP-1 should not only inhibit the growth of *Streptococcus iniae* but also can kill the bacterial cells. Therefore, it is concluded that the bacteriophage Str-INP-1 can be used as an active ingredient of the composition in order to prevent the infections of *Streptococcus iniae*.

Example 5: Therapeutic Effect of Bacteriophage Str-INP-1 on the Infections of *Streptococcus iniae*

Therapeutic effect of the bacteriophage Str-INP-1 on the olive flounder suffered from streptococcosis by the infections of *Streptococcus iniae* was investigated. Particularly, total 2 groups of juvenile olive flounder (50 juvenile olive flounder per group, body length 6~9 cm) at 4 months old were prepared, which were cultured separately in different water tanks for 14 days. Surrounding environment of the water tanks was controlled. The temperature and humidity in the laboratory where the water tanks stayed were also controlled. From the 5$^{th}$ day of the experiment, feeds adding *Streptococcus iniae* cells at $1\times10^8$ cfu/g were provided twice a day for 3 days according to the conventional feed supply procedure. Olive flounder subjects showing clinical symptoms of streptococosis from the last day of this procedure, were observed in both water tanks. From the next day of providing feeds adding *Streptococcus iniae* cells for 3 days (the 8$^{th}$ day of the experiment), olive flounder of the experimental groups (adding the bacteriophage) were fed with feeds adding the bacteriophage Str-INP-1 at $1\times10^8$ pfu/g according to the conventional feed supply procedure, while olive flounder of the control group (without the bacteriophage) were fed with the same feeds without adding the bacteriophage Str-INP-1 according to the conventional procedure. After the 8$^{th}$ day of the experiment, all the test animals were examined whether being suffered from streptococcosis or not. The outbreak of streptococcosis was detected by measuring body darkening index. The measurement of body darkening index was performed by the conventional method obtaining Dark Coloration (DC) score (0: normal, 1: light coloration, 2: dark coloration). The results are shown in Table 2.

TABLE 2

Dark coloration score (average values)

| Days | D 8 | D 9 | D 10 | D 11 | D 12 | D 13 | D 14 |
|---|---|---|---|---|---|---|---|
| Control group (−bacteriophage) | 1.04 | 1.40 | 1.64 | 1.72 | 1.68 | 1.36 | 1.16 |
| Experimental group (+bacteriophage) | 1.00 | 0.84 | 0.32 | 0.20 | 0.12 | 0.08 | 0.04 |

From the above results, it is confirmed that the bacteriophage Str-INP-1 of the present invention could be very effective to treat the infection of *Streptococcus iniae*.

Example 6: Preparation of Feed Additives and Feeds

Feed additives were prepared by adding the bacteriophage Str-INP-1 solution at the concentration of $1\times10^8$ pfu/g feed additives. The preparation method thereof was as follows: Maltodextrin (40%, w/v) was added to the bacteriophage solution and then trehalose was added to reach 10 weight %. After mixing well, the resulting mixture was freeze-dried. Lastly, the dried mixture was grinded into fine powders. The drying procedure above can be replaced with drying under a reduced pressure, drying at warm temperature, or drying at room temperature. To prepare the control for comparison, feed additives that did not contain the bacteriophage but contained only buffer (10 mM Tris-HCl, 10 mM $MgSO_4$, 0.1% Gelatin, pH 8.0) were prepared.

The above two kinds of feed additives were mixed with raw fish-based moist pellet at the volume of 250 times the volume of additives, resulting in two kinds of final feed additives.

Example 7: Preparation of an Immersion Agent (Medicine Bath Agent)

An immersion agent comprising $1\times10^8$ pfu/ml of bacteriophage Str-INP-1 was prepared. The preparation method was as follows: $1\times10^8$ pfu of the bacteriophage Str-INP-1 was added to 1 ml of buffer, which was well mixed. To prepare the control, the buffer itself that is the same with the one used for the mixture of the bacteriophage solution was prepared.

The prepared two kinds of immersion agents were diluted with water at the ratio of 1:1,000, resulting in the final immersion agents for the experiment.

Example 8: Effect on Olive Flounder Aquafarming

The effect of the feeds and the immersion agents prepared in Example 6 and Example 7 on olive flounder aquafarming was investigated. Particularly, the investigation was focused on the mortality. Total 600 olive flounder were grouped into two, 300 olive flounder for each group, which proceeded to the following experiment (group A; fed with feed, group B; treated with immersion agent). Each group was divided to two sub-groups again, group of 150 olive flounder each (sub-group-①: treated with the bacteriophage Str-INP-1, sub-group-②: not-treated with the bacteriophage Str-INP-1). The olive flounder used for this experiment were the juvenile olive flounder at 4 months old. Each sub-group olive flounder were aquacultured in separate water tanks placed at a certain space interval. Each sub-group was distinguished and named as shown in Table 3.

TABLE 3

Sub-groups of aquafarming experiment of olive flounder

| Treatment | Sub-group | |
| --- | --- | --- |
| | Treated with the bacteriophage Str-INP-1 | Not-treated with the bacteriophage |
| Fed with feeds | A-① | A-② |
| Treated with immersion agents | B-① | B-② |

Feeds were provided according to the conventional feed supply procedure as presented in Table 3 with the feeds prepared as described in Example 6. The treatment of immersion agent was also performed by the conventional procedure as presented in Table 3 with the immersion agent prepared as described in Example 7. The test result is shown in Table 4.

TABLE 4

Mortality of olive flounder in aquafarming

| Group | Dead fish/total test fish (No.) | Mortality (%) |
| --- | --- | --- |
| A-① | 6/150 | 4.0 |
| A-② | 37/150 | 24.7 |
| B-① | 8/150 | 5.3 |
| B-② | 43/150 | 28.7 |

The above results indicate that the feeds prepared by the present invention and the immersion agent prepared according to the present invention are effective to reduce the mortality of the cultured olive flounder. Therefore, it is concluded that the composition of the present invention could be efficiently applied to improve outcomes of olive flounder aquaculture.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A pharmaceutical composition for inhibiting or treating the infections of *Streptococcus iniae* comprising an effective amount of a Siphoviridae bacteriophage Str-INP-1 as an active ingredient, wherein said Siphoviridae bacteriophage is isolated from the nature and can kill *Streptococcus iniae* cells specifically, wherein the genome of said Siphoviridae bacteriophage comprises the nucleotide sequence of SEQ. ID. NO: 1, and wherein said pharmaceutical composition is formulated in the form of a bath treatment agent or a feed additive.

2. A method for inhibiting or treating the infections of *Streptococcus iniae* in a subject in need thereof, which comprises administering to the subject a therapeutically effective amount of the pharmaceutical composition as set forth in claim 1.

* * * * *